(12) United States Patent
Deshmukh

(10) Patent No.: US 8,109,961 B2
(45) Date of Patent: Feb. 7, 2012

(54) BONE FUSION SYSTEM AND METHOD

(76) Inventor: Vinay Deshmukh, Charlotte, NC (US)

( * ) Notice: Subject to any disclaimer, the term of this patent is extended or adjusted under 35 U.S.C. 154(b) by 1128 days.

(21) Appl. No.: 11/616,675

(22) Filed: Dec. 27, 2006

(65) Prior Publication Data

US 2008/0161649 A1 Jul. 3, 2008

(51) Int. Cl.
*A61B 17/00* (2006.01)
(52) U.S. Cl. ........................................ 606/190
(58) Field of Classification Search .......... 600/201, 600/190, 210, 217, 235; 241/199.12, 606, 241/30; 604/46–86, 272, 540; 606/92–94; *A61B 1/32, 1/267, 17/20; B02C 19/00; A61M 37/00, 31/00, 5/32, 1/00*
See application file for complete search history.

(56) References Cited

U.S. PATENT DOCUMENTS

| | | | | |
|---|---|---|---|---|
| 2,688,470 A * | 9/1954 | Marco | | 366/155.2 |
| 2,844,176 A * | 7/1958 | Barrows et al. | | 241/188.1 |
| 4,095,751 A * | 6/1978 | Artin | | 241/37.5 |
| 4,610,243 A * | 9/1986 | Ray | | 600/206 |
| 5,743,853 A * | 4/1998 | Lauderdale | | 600/210 |
| 6,171,299 B1 * | 1/2001 | Bonutti | | 606/1 |
| 6,824,087 B2 * | 11/2004 | McPherson et al. | | 241/30 |
| 7,044,051 B2 * | 5/2006 | Le Rouzic | | 99/512 |
| 7,422,361 B2 * | 9/2008 | Pryor et al. | | 366/197 |
| 2002/0138145 A1 * | 9/2002 | Marchosky | | 623/17.13 |
| 2003/0061944 A1 * | 4/2003 | Fouquet | | 99/511 |
| 2004/0010260 A1 * | 1/2004 | Scribner et al. | | 606/93 |
| 2004/0147812 A1 * | 7/2004 | Hamel | | 600/213 |
| 2005/0173573 A1 * | 8/2005 | Hay et al. | | 241/199.12 |
| 2009/0209827 A1 * | 8/2009 | Shelokov | | 600/205 |
| 2010/0004653 A1 * | 1/2010 | Rasekhi | | 606/85 |

* cited by examiner

*Primary Examiner* — Eduardo C Robert
*Assistant Examiner* — Tara Carter
(74) *Attorney, Agent, or Firm* — Husch Blackwell LLP

(57) ABSTRACT

A bone fusion system and method is disclosed. The system includes a bone mill having at least one docking station that is located at a position other than where a user inserts bone to be morcellated into the bone mill. This allows, for example, a surgeon to deposit morcellated bone onto a desired location on a patient's spine immediately after the bone is morcellated. The bone mill can include two or more docking stations having different sizes so that a surgeon can couple differently sized syringes to the bone mill. This allows, for example, morcellated bone to be deposited at two or more locations immediately after the bone is morcellated. A hand held retractor having a serrated tip is included so that a surgeon can simultaneously retract a patient's muscle bundles while decorticating a recipient bed.

25 Claims, 2 Drawing Sheets

BONE FUSION SYSTEM AND METHOD

BACKGROUND OF THE INVENTION

The present invention generally relates to the field of bone fusion and, more particularly, to a system and method for performing bone fusion.

Spinal fusion is one method for treating spinal fractures and other injuries and diseases of the spine. Spinal fusion is a procedure performed by linking the two vertebras spanning the cartilaginous disc. The fusion procedure thereby either repairs the broken bone or eliminates the degenerated joint.

Spinal fusion is one method for treating spinal fractures. Spinal fusion is a procedure performed by linking the two vertebras spanning the cartilaginous disc. The fusion procedure thereby either repairs the broken bone or eliminates the degenerated joint.

Postero-lateral fusion is the most common type of spinal fusion operation that is performed. The process of postero-lateral fusion usually begins with the harvesting and handling of a bone graft and the preparation of a recipient transverse processes using a drill or a sharp awl. Typically, the bone graft is harvested within no more than 30 minutes of planned use thereby increasing the importance of efficiency during the surgical procedures. The graft also is kept moist in a saline or blood-soaked sponge before use.

The second step in postero-lateral fusion is the preparation of the recipient bed. The fusion bone to be placed in the fusion bed morcellated, either by hand or with a bone mill. An assistant then retracts the large muscle bundles in the back to expose the transverse processes and the postero-lateral space.

Areas of the recipient bed where there is planned fusion should be decorticated, which allows contact of the graft with cancellous bone while avoiding weakening the structure of the recipient bed with overzealous destruction of the cortical bone. It is imperative that preparation of the recipient bed be undertaken with utmost care because it protects the viability of the tissues that will serve as the primary source of the cellular components required for fusion. After the recipient fusion bed has been decorticated, the surgeon then deposits the morcellated fusion bone into the space piece by piece.

There are many drawbacks with current fusion methodologies. For example, in some cases the fusion bone is broken into small pieces by hand. This can be manually fatiguing and difficult for the surgical assistant. Additionally, it can occupy the surgical assistant and therefore impede their ability to assist the surgeon with the ongoing surgery.

U.S. Pat. No. 6,824,087 issued on Nov. 30, 2004, and is entitled "automatic bone mill." Column 2, lines 31-34 and column 6, lines 29-32 of the patent state that an opening in a bone mill through which human bone is inserted into the bone mill can also be used to connect to a device such as a syringe for receiving milled bone from the bone mill. The content of this patent is incorporated by reference into this application as if fully set forth herein.

The device disclosed in the '087 patent has drawbacks. For example, by requiring a user to affix a syringe to the same opening in which bone is inserted into the device, a time delay is necessarily introduced before the milled bone can be inserted into a patient, which can have deleterious effects on the efficacy of the fusion procedure. Additionally, for example, the '087 patent contains no disclosure as to the ability to simultaneously use different sized syringes to withdraw milled bone and then simultaneously deposit the milled bone at different surgical sites that have different size requirements. It is important to minimize the time from when bone is harvested to when it is deposited at a surgical site, which is something that is not taught by the '087 patent.

Another drawback with some current procedures is the manner in which the recipient bed is prepared. The drill or awl used to prepare the transverse process must be placed with great accuracy to avoid injury to the surrounding soft-tissue structures. This requires greater effort at retracting the paraspinous muscle bundles that cover the bone. This process can be difficult and may result in greater post-operative discomfort to the patient.

Additionally, the current manner in which the bone is placed onto the recipient bed has a number of drawbacks. For example, under a current method, the assistant must perform the lengthy and arduous task of retraction of the patient's muscle bundles. Additionally, the bit by bit method of bone placement is exacerbating to the surgeon, and often results in a diminished and inadequate volume of bone placed into the gutter.

SUMMARY OF THE INVENTION

The present invention provides a unique bone fusion system and method. In an exemplary embodiment, the invention includes a bone mill that is provided with at least one docking station that is located at a position other than where a user inserts bone to be morcellated into the bone mill. This allows, for example, a surgeon to deposit morcellated bone onto a desired location on a patient's spine immediately after the bone is moresellated.

Another unique feature of the present invention is that, for example, two or more docking stations of different sizes can be provided on the bone mill. This allows, for example, a surgeon to operatively couple different sized syringes to the bone mill at the same time and, therefore, to place morcellated bone at two or more locations immediately after the bone is morcellated. This is desirable to allow a surgeon to use, for example, a small syringe to access tight recipient beds within a patient.

Another unique feature of the present invention is, for example, the use of a hand reactor with a curved and serrated tip. This allows, for example, a patient's muscle groups to be retracted while simultaneously scraping and decorticating the transverse process; a series of syringes ergonomically designed to allow for direct injection of large volumes of bone into the fusion space.

BRIEF DESCRIPTION OF THE DRAWINGS

Various examples of objects, features and attendant advantages of the present invention will become fully appreciated as the same becomes better understood when considered in conjunction with the accompanying drawings, in which like reference characters designated the same or similar parts throughout the several views, and wherein.

DETAILED DESCRIPTION OF THE INVENTION

Figure 1:
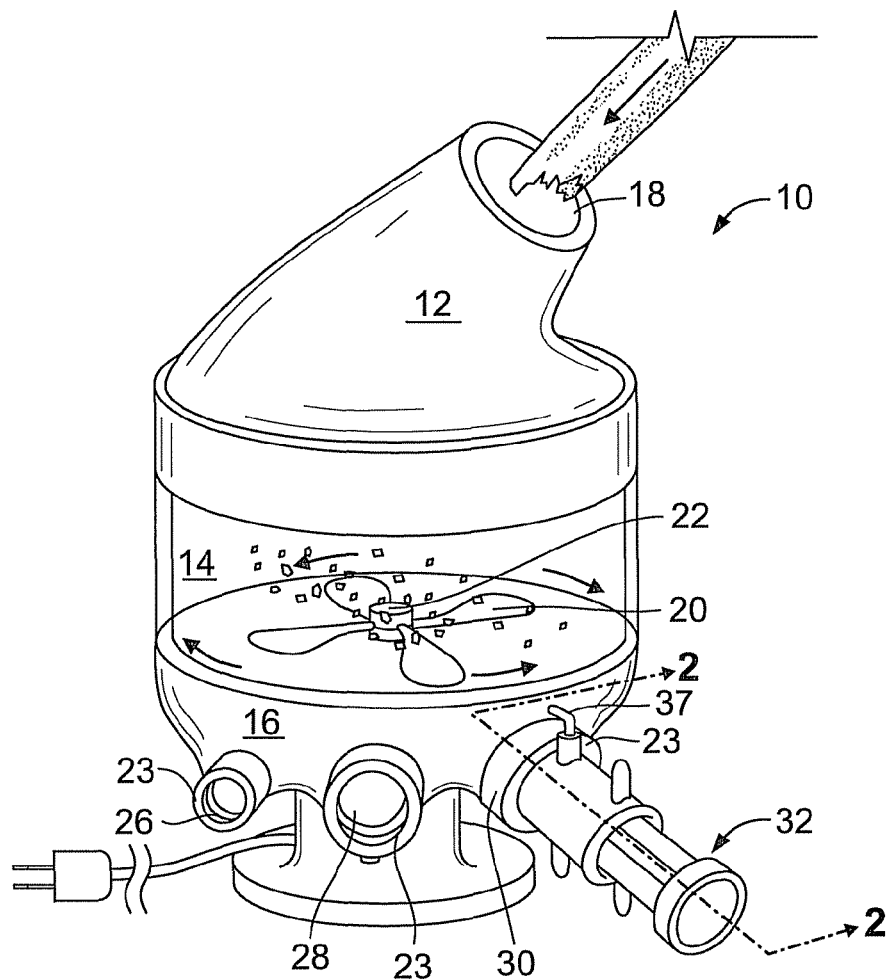
FIG. 1 illustrates an exemplary embodiment of a bone mill with three docking ports.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated. It should be further understood that the title of this section of this specification, namely, "Detailed Description Of The Invention", relates to a requirement of the United States Patent Office, and does not imply, nor should be inferred to limit the subject matter disclosed herein.

In the present disclosure, the words "a" or "an" are to be taken to include both the singular and the plural. Conversely, any reference to plural items shall, where appropriate, include the singular.

Referring now to FIG. 1, an exemplary embodiment of a bone mill 10 that incorporates aspects of the present invention is shown. In accordance with this embodiment, bone mill 10 includes a top cap 12, a cylindrical middle section 14, and a bottom piece 16, all of which are fitted together by suitable means such as, for example, a detachable interference fit between each component. The middle section can, if desired, be integrally formed as a portion of either the bottom section 16 or the top cap 12.

Top cap 12 includes an opening 18 through which a user can insert pieces of human bone as shown. The bone mill 10 includes a set of chopping blades 20 that are rotated by a motor (not shown) about a central axis of hub 22. While bone mill is preferably motor powered, alternative designs with, for example, a hand crank or air powered morcellating mechanism also are contemplated. The rotation of the blades 20 morcellates the bones pieces that are inserted through the opening 18, and creates an airflow which causes the moresellated bone to be deposited in a reservoir 24 that is defined within bottom piece 16.

One aspect of the present invention is that it includes, for example, at least one syringe docking station 23 that is located at a position on the bone mill 10 that is different from the opening 18 through which bone is inserted by a user. In the embodiment of the invention illustrated in FIG. 1, three syringe docking stations 26, 28 and 30 are illustrated. Significant advantages are obtained by locating the syringe docking stations away from the opening 18. This allows, for example, the time between bone morcellation and deposition at a surgical site to be minimized, which increases the efficacy of the bone fusion treatment.

A second aspect of the present invention is that two or more syringe docking stations can be provided in the bottom section 16. One advantage of this is that, for example, the two or more syringe docking stations can be made of different sizes so that different sizes syringes can be attached thereto. This is desirable, for example, because the size of a syringe can be matched to the type of bone fusion procedure that is needed to be done. For example, a small syringe with a long tip is necessary for a surgeon to deposit morcellated bone in certain locations on a patient's spine.

In a preferred embodiment of the present invention, a first docking station 30 is designed to engage a large diameter syringe 32 as shown in FIG. 1. The second and third docking stations 26 and 28 are designed to engage a medium and small diameter syringe (not shown). While the bone mill 10 is being used, the docking stations 26, 28 and 30 can be covered, for example, with plastic caps (not shown). In a preferred embodiment, other mechanisms such as, for example, a stopcock can be incorporated into each docking station to prevent morcellated bone from exiting the docking stations.

Figure 2:
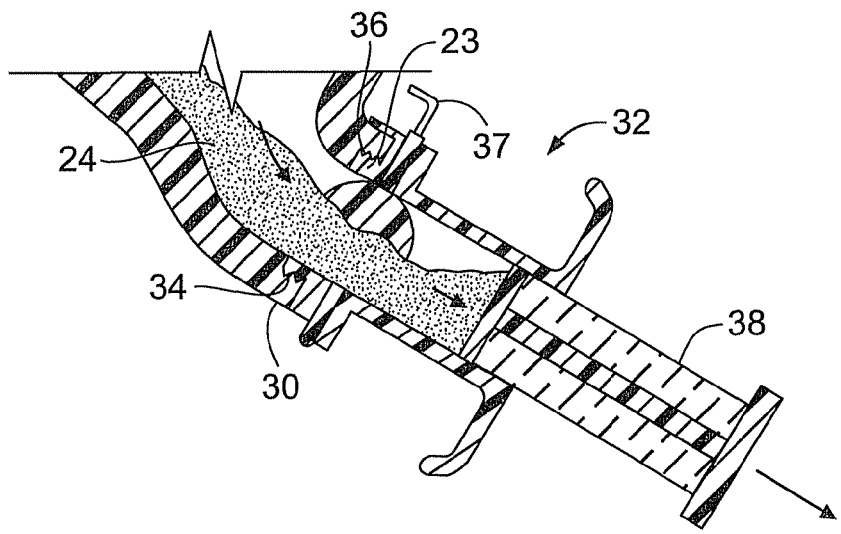
FIG. 2 illustrates an exemplary embodiment of a custom designed syringe which allows direct injection of large volumes of bone into fusion space.

Referring to FIG. 2, a cross-sectional view of a syringe 32 that is operatively engaged with docking station 30 is shown. In this embodiment of the present invention, syringe 32 includes a threaded tip 34 that engages corresponding threads 36 that are defined in the docking station 30. The present invention is not limited to a thread based connection between the syringe 32 and the docking station 30. For example, the outer diameter of a distal end of the syringe 32 could be appropriately sized to allow the syringe 32 to be detachably interference fitted into docking station 30.

After a user has deposited a desired quantity of bone into the bone mill 10, and after the bone has been morcellated, a user can cause the morcellated bone to be aspirated in the syringe 32. In accordance with one embodiment of the present invention, a user rotates the stopcock 37 to an open position, and then withdraws plunger 38 to create a vacuum. The vacuum causes the morcellated bone to be draw into syringe 32. After a desired quantity of moresellated bone is received with the syringe 32, a surgeon can utilize the syringe 32 to, for example, deposit morcellated bone onto a recipient bed.

The syringe 32 can have, for example, a blunt tip as shown in FIG. 2. Preferably, the syringe 32 is ergonomically designed to allow for the direct injection of large volumes of bone into a fusion space. Syringe 32 also preferably is disposable and, for example, be manufactured of a suitable plastic material.

Syringe 32 can be designed to have any desired shape to allow for different placements of bone grafts. For example, a small diameter syringe is ideal for placement of bone into the intervertebral space, and a tapered syringe is ideal for placement of bone through minimally invasive exposures. A large diameter syringe is useful for deposition of bone into the postero lateral gutter, which is the anatomic space on either side of the back portion of the vertebra. However, it should be noted that the size of the syringe and its usage are largely matters of the surgeon's choice and comfort level, and syringes of varying sizes may be employed for a multitude of different procedures where appropriate.

In accordance with specific embodiments of the present invention, a syringe that is used for fusing the intervertebral disc can have a diameter of 7 mm, a length of 13 cm, and a plunger length of 14.5 cm. A syringe used for the posterolateral space would have a diameter of 12 mm, with a syringe length of 13 cm and a plunger length of 14.5 cm. It should be emphasized that such specific examples merely are examples, and should not be used to limit the scope of the invention disclosed and claimed herein.

The bone mill 10 can be constructed to have other features to maximize its efficient in the operating room. For example, a disposable liner (not shown) can be fitted with the bottom piece 16 so that, after the bone mill 10 is used in a surgical procedure, the liner can be replaced with a new liner to thereby allow the bone mill to be reused quickly.

Figure 3:
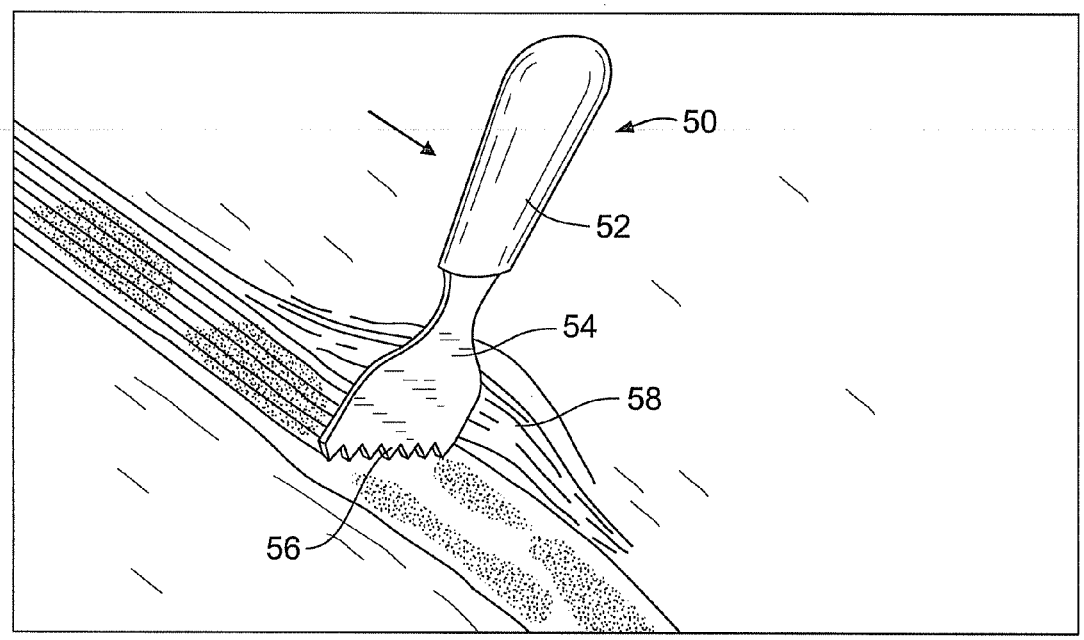
FIG. 3 illustrates a hand held retractor with a serrated retractor tongue for decortication of a recipient bed.

Another aspect of the present invention is the utilization of a device that allows a patient's muscles to be retracted simultaneously with the decortication and preparation of the recipient bed. Referring to FIG. 3, a perspective view of a hand held retractor 50 that can be used for surgical retraction purposes is shown. The retractor 50 includes a handle 52 that can be of any desired size or shape. In accordance with one aspect of the invention, the retractor 50 includes an angled head portion 54 as shown that is particularly well suited for low-profile surgical applications. However, the head portion 54 can be of any desired magnitude and curvature as necessary for a particular surgical environment. For example, in alternative embodiments the head portion 54 can be straight, slightly angled or even shaped like a spoon. The retractor 50 also includes a serrated tip 56. In a specific embodiment, the retractor 50 is made of stainless steel, and has a large diameter generally cylindrical handle 52 that provides for easy gripping.

Figure 4:
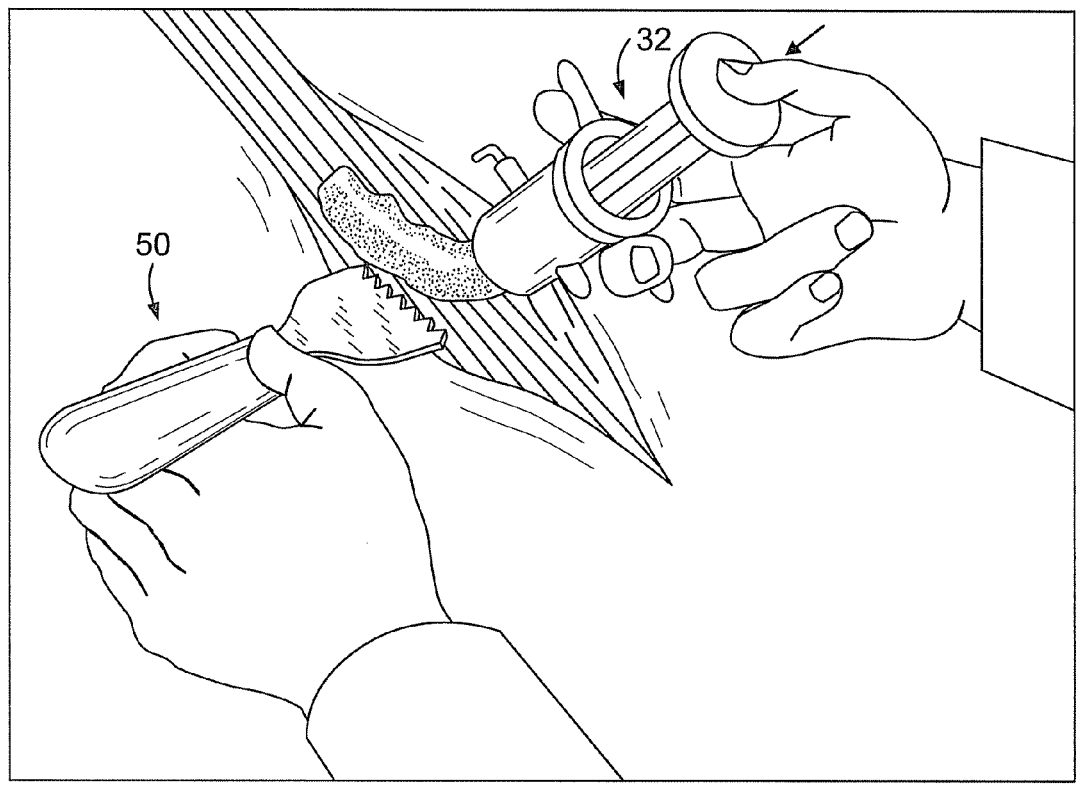
FIG. 4 illustrates a view of an exemplary surgical procedure wherein a surgeon uses the hand held retractor shown in FIG. 3 to retract muscle bundles and decorticate a recipient bed while simultaneously depositing morcellated bone thereon.

The tip 56 is serrated to allow, for example, the surgeon to scrape and decorticate the transverse process of the patient. While the tip 56 scrapes and decorticates the transverse process, the angled portion 54 retracts and holds the muscle bundle 58 to expose the fusion bed for placement of the fusion bone as, for example, shown in FIG. 4. This provides improved accuracy in preparing the transverse process and retracting the muscle bundle. The invention contemplates a wide variation of serration design, including variations in the number of serrations, length of serrations and style of serration teeth. For example, six different serrations can be defined in the tip 54.

From the foregoing it will be observed that numerous modifications and variations can be effectuated without departing form the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A combination, comprising:
    a bone mill including a bone mill body having at least one opening through which bone may be introduced into the bone mill, a reservoir for morcellated bone, and at least one syringe docking station from which morcellated bone may be aspirated from the bone mill reservoir into a syringe by action of pulling a plunger of the syringe out from the syringe;
    a milling element for morcellation of bone, the milling element being operatively located between the bone introduction opening and the at least one syringe docking station;
    each of the at least one syringe docking stations being designed specifically to engage a syringe, of a particular diameter and having a tip that is structured and adapted to be physically coupled to one of the at least one syringe docking stations; and
    wherein the at least one syringe docking station is physically separate from the bone introduction opening on the bone mill when the bone mill is in operation.

2. The combination of claim 1, further comprising a hand held retractor including a retractor tongue, a serrated tip being defined on a distal end of the serrated tongue so that a user of the hand retractor can decorticate and prepare a recipient site for deposition of morcellated bone while simultaneously retracting muscle tissue to expose the recipient bed.

3. The combination of claim 2, wherein the tip of the retractor is curved.

4. The combination of claim 2, wherein the retractor is comprised of stainless steel.

5. The combination of claim 1, wherein the the at least one syringe docking station comprises at least two syringe docking stations.

6. The combination of claim 5, wherein two of the at least two syringe docking stations are designed to engage syringes of different diameters, respectively.

7. The combination of claim 1, wherein the bone mill includes a disposable liner.

8. The combination of claim 1, wherein the syringe is disposable.

9. The combination of claim 1, wherein the syringe is formed from a plastic material.

10. The combination of claim 1, wherein the syringe is sized to allow morcellated bone to be deposited into a postero-lateral fusion space.

11. The combination of claim 1, wherein the syringe is sized to allow placement of morcellated bone into an intervertebral space.

12. The combination of claim 1, wherein a distal end of the syringe is tapered.

13. A method, comprising the steps of:
    utilizing a bone mill to morcellate an amount of human bone, the bone mill including a bone mill body having at least one opening through which bone may be introduced into the bone mill, a reservoir for morcellated bone, at least one syringe docking station from which morcellated bone may be aspirated from the bone mill reservoir into a syringe by action of pulling a plunger of the syringe out from the syringe., and a milling element for morcellating bone, the milling element being operatively located between the bone introduction opening and the at least one syringe docking station;
    coupling a syringe, of a particular diameter and having a tip that is structured and adapted to be physically coupled to one of the at least one syringe docking stations, to one of the at least one syringe docking stations that is designed specifically to engage a syringe of the particular diameter;
    using the syringe to withdraw morcellated bone from the bone mill and into a chamber defined within the syringe; and
    wherein the at least one syringe docking station is physically separate from the bone introduction opening on the bone mill when the bone mill is in operation.

14. The method of claim 13, further comprising the step of using a hand held retractor to simultaneously retract a muscle bundle and decorticate a recipient bed of a patient.

15. The method of claim 14, wherein the retractor includes a serrated tongue, a serrated tip being defined on a distal end of the serrated tongue.

16. The method of claim 15, wherein the tip of the retractor is curved.

17. The method of claim 14, wherein the retractor is comprised of stainless steel.

18. The method of claim 13, wherein the the at least one syringe docking station comprises at least two syringe docking stations.

19. The method of claim 18, wherein two of the at least two syringe docking stations are designed to engage syringes of different diameters, respectively.

20. The method of claim 13, wherein the bone mill includes a disposable liner.

21. The method of claim 13, wherein the syringe is disposable.

22. The method of claim 13, wherein the syringe is formed from a plastic material.

23. The method of claim 13, wherein the syringe is sized to allow morcellated bone to be deposited into a postero-lateral fusion space.

24. The method of claim 13, wherein the syringe is sized to allow placement of morcellated bone into an intervertebral space.

25. The method of claim 13, wherein a distal end of the syringe is tapered.

* * * * *